United States Patent [19]

Drake

[11] Patent Number: 4,611,400

[45] Date of Patent: Sep. 16, 1986

[54] BLADE AND PROCESS OF MAKING SAME

[76] Inventor: Anthony F. Drake, P.O. Box 31192, Santa Barbara, Calif. 93130-1192

[21] Appl. No.: 696,810

[22] Filed: Jan. 31, 1985

Related U.S. Application Data

[62] Division of Ser. No. 388,547, Jun. 15, 1982, abandoned.

[51] Int. Cl.⁴ .............................................. C03B 33/02
[52] U.S. Cl. ................................... 30/353; 76/104 R; 125/23 R; 225/1; 225/93; 225/103
[58] Field of Search ............... 225/1, 2, 93, 103, 96.5; 125/23 R; 76/101 D, 104 R; 30/346.53, 346, 353

[56] References Cited

U.S. PATENT DOCUMENTS

| 3,494,521 | 2/1970 | Hellström | 225/104 X |
| 3,819,096 | 6/1974 | Pyper | 225/104 X |
| 4,256,246 | 3/1981 | Kindel | 225/103 |

Primary Examiner—Frank T. Yost

[57] ABSTRACT

A single or multi-edge blade including a fractured edge. The blade can be oriented to be left-handed, right-handed, or two-sided. The size, shape and sharpness of the blade are a function of controlled variables during fracturing. The sharpness of the blade occurs along and at a molecular level in a controlled process, dependent upon the material and the predetermined variables of fracturing. The blade can consist of glass, crystalline, non-crystalline, composite or like materials. The process of fracturing the material is through controlled pressure at discrete angles over a defined area with predetermined force during a specific time interval.

9 Claims, 27 Drawing Figures

BLADE AND PROCESS OF MAKING SAME

CROSS REFERENCE TO CO-PENDING APPLICATIONS

This is a division of application Ser. No. 388,547, filed on 6-15-82, now abandoned.

BACKGROUND OF THE INVENTION

1. Field of the Invention

The present invention pertains to a fractured blade and, more particularly, pertains to a blade scalpel for surgery.

2. Description of the Prior Art

Prior art blades such as glass have exhibited numerous problems over the years. Prior art glass blades had ground cutting edges or acid-etched cutting edges which provided an edge which was rough, had a finite thickness, and were not sharp. Consequently, the cutting edge displaced tissue during cutting. This displaced tissue decreased the healing rate and increased the likelihood of infection along the incision. Further, the ground, honed or polished cutting edges provided residue on the cutting edge or substantially adjacent to the cutting edge which was less than desirable.

The prior art ground or polished edges produced edges which were microscopically and sometimes visually rough, irregular and thick. The cutting edges when used as surgical instruments produced incisions which were microscopically rough and irregular.

The prior art manually-generated blades are less than suitable for microsurgery. Microsurgery requires the finest, sharpest blades available for repairing of nerves, etc., and such prior art blades have been unable to meet the needs of this type of surgery.

The present invention overcomes the disadvantages of the prior art by providing a fractured blade of a material such as glass or like material possessing a fractured edge which is thin and substantially perfectly sharp.

SUMMARY OF THE INVENTION

The general purpose of the present invention is to provide a blade of glass, crystalline, non-crystalline, or composite fracturable material providing a thin, sharp edge when fractured with predetermined parameters including velocity, pressure, and an angle for a specific material over time. The material can be glass, a crystalline material, a non-crystalline material, or a composite material. The preferred glass or like blade is produced from a core of material under pressure at predetermined parameters provided by, for example, a system of a hydraulic press. A core of material can be fractured for one edge or a plurality of edges for specific geometrical blade orifices about the length of the material, the fractured blade then being sliced and attached to handles for use as scalpels. The material of the blade can also be of elements as naturally found.

According to one embodiment of the present invention there is provided a blade having a fractured edge, the fractured edge or fractured edges being along the length of the blade culminating in either a rectangular end, an oval end, a sharp end, a trapezoidal end or the like, having at least one or a plurality of finite sharp edges. The fracture is initiated and propagates through the material forming the sharp and smooth edge. The fracture occurs along a molecular level providing a clean, smooth, thin and sharp cutting edge to the blade.

The cross section of the blade can be triangular, trapezoidal, multi-sided, or other cross-sectional surfaces which are within the scope of this patent including plano-convex, substantially planar, etc. The faces of the blade can take any geometrical configuration.

Depending upon the geometrical configuration of the point of the blade and the angle of fracturing, the fractured edges can likewise assume any geometrical configuration, which of course corresponds to that configuration of the blade. While the blade can be planar, the blade can also have a degree of curvature through any of the axes of the body of the blade.

Process for fracturing the blades can be performed by a hydraulically operated press which controls variable predetermined parameters while holding the core of the material during fracturing mechanically stable and under zero vibration.

According to an additional embodiment of the present invention, there is provided an illuminated blade, preferably glass blade, where a longitudinal slot or hole is positioned in the handle up to and adjacent the junction of the blade and handle, and includes an illuminating source within the handle positioned adjacent to the junction. The illuminating source can be either a fiber optic cable of either a stranded or cable bundle, or an actual illuminating device such as an LED or grain-of-wheat lamp. The power source can be either internal through the handle or, more likely, through a power cable to an external illuminating or power source.

The blades are interchangeable into an interchangeable handle likened to replacement of razor blades. Interchangeable blades provide a choice and selection of a plurality of different fractured edges for surgery which are suitable for a single holder and/or purposes of sterilizing.

A significant aspect and feature of the present invention is a blade for use such as a scalpel in surgery which incorporates a fractured edge which is smooth and sharp. The fractured edge provides a cutting edge which has not been chemically bonded or polished with residual materials, and also presents a fractured edge which is thin and sharp. The use of such materials is unique and beneficial to the patient.

Another significant aspect and features of the present invention is a blade which is manufactured by fracturing material under controlled parameters, pressure and angular relation between the fracturing tool and the core of the material being fractured. Fracturing of material when all the parameters are accounted for provides for processing of fractured edges which are sharp and smooth.

An additional significant aspect and feature of the present invention is a blade having a fractured edge including a predetermined geometrical configuration of the edge and end with respect to the opposing faces of the body of the blade. The blade edge can assume a planar, rounded, pointed, etc. edge about planar, concave, etc. faces of the blade body.

Still another significant aspect and feature of the present invention is a blade including a transparent or translucent body which is illuminated by a source such as a fiber optic or LED in the blade handle. The light source can be color coded for the type of surgical blade or for the intended surgical use.

Further significant aspects and features of the present invention are fracturing a plurality of blades from a core of material of a predetermined geometrical configuration. Each fractured blade includes a predetermined geometrical configuration of the blade body and of the fractured edge.

Depending upon the predefined circumstances of the body of the core of material, the blade can be fractured repetitively from the same core of material with like geometrical body and edge configurations.

According to another embodiment of the present invention, there is provided a spring-actuated blade-cutting tool for the dicing of substantially planar blades into predetermined lengths. The blade-cutting tool is a spring-actuated hand-held device.

According to an additional embodiment of the present invention, there is provided a rotating blade having a substantially circular configuration analogized to a rotating disc with a predetermined cutting edge similar to that previously disclosed, the blade rotating in a suitable scalpel handle which can be either manually driven or gear driven through known gear and drive mechanisms similar to dental tools where the blade is utilized for the incisions of tough tissue, cartilage and bone. The rotating disc blade requires less displayed tissue, decreases scar tissue, and less hand fatigue in making incisions through tougher tissue. The cutting edge of the rotating disc is a fracture edge, similar to that as discussed above, and lends itself to the same principles of this patent.

An additional significant aspect and feature of the present invention is a blade-cutting tool for cutting the planar segments of the blade into predetermined lengths. Planar segments of the blade include blades which have a longitudinal axis regardless of geometrical surfaces of the faces or the ends of the particular blade geometry. The tool is intended for cutting blades to desired lengths for insertion into scalpel handles.

Still another significant aspect and feature of the present invention is a rotating circular disc blade in a yoke of a scalpel handle where the rotating disc can be either manually moved or mechanically powered by air or the like motor means. The rotating disc is particularly beneficial for the incision of tough tissue, cartilage, muscle, or bone as required.

A significant aspect and feature of the present invention is a blade for use such as a scalpel in surgery which incorporates a fractured edge which is smooth and sharp. The fractured edge provides a cutting edge which has not been chemically honed or polished with residual materials, and also presents a fractured edge which is thin and sharp.

Another significant aspect and feature of the present invention is a blade which is manufactured by fracturing material under controlled parameters, pessure and angular relation between the fracturing tool and the core of the material being fractured. Fracturing of material when all the parameters are accounted for provides for processing of fractured edges which are sharp and smooth.

An additional significant aspect and feature of the present invention is a blade having a fractured edge including a predetermined geometrical configuration of the edge and end with respect to the opposing faces of the body of the blade. The blade edge can assume a planar, rounded, pointed, etc. edge about planar, concave, etc. faces of the blade body.

Still another significant aspect and feature of the present invention is a blade including a transparent or translucent body which is illuminated by a source such as a fiber optic or LED in the blade handle. The light source can be color coded for the type of surgical blade or for the intended surgical use.

Further significant aspects and features of the present invention are fracturing a plurality of blades from a core of material of a predetermined geometrical configuration. Each fractured blade includes a predetermined geometrical configuration of the blade body and of the fractured edge.

Depending upon the predefined circumstances of the body of the core of material, the blade can be fractured repetitively from the same core of material with like geometrical body and edge configurations.

Having thus described embodiments of the present invention, it is the principal object hereof to provide a blade with at least one fractured edge about a defined geometrical body.

An object of the present invention is to provide a blade having a fractured edge which is smooth, sharp and thin.

Another object of the present invention is to provide a blade having a fractured edge, or a plurality of fractured edges; the fractured edges assuming the geometrical plane or curvature of the body of the blade itself. The geometrical material can have either a planar body or a curved body or the like dependent upon the molecular structure of the material.

A further object of the present invention is a blade having either a planar edge, a curved edge, or a pointed edge or any like geometrical shape about a geometrical body.

An additional object of the present invention is to provide a glass blade having a fractured edge which is smooth, sharp and thin. The blade can have any desired point, one or more edges and have any desired opposing geometrical body configured surfaces. The blade can be permanently affixed to the handle, or can be mechanically secured to an interchangeable handle. The blade can also be illuminated with white light or colored light for either signifying the type of blade or the type of surgery the blade is to be utilized in. The blade can also be secured into a heat formed socket.

Still another object is to provide an illuminated transparent or translucent blade through a low-power light source in the handle adjacent the junction of the handle-blade body for illuminating the blade as well as the surrounding and adjacent area of surgical incision by the blade.

A further object of the present invention is to provide a blade with a fractured edge which is interchangeable with other blades where the geometrical body configuration of the interchangeable blades is substantially similar.

A still further object of the present invention is a blade having an extremely sharp fractured edge which particularly lends itself to pecise delicate surgery. While the blade is intended for any type of surgery, the blade is particularly suited to the more definitive areas of neurosurgery or ophthalmologic surgery. Other areas of surgery include plastic, cosmetic, and heart as well as other areas as deemed useful.

Glass, crystalline, non-crystalline and composite materials are representative materials of the blade. Other like materials can be utilized including materials which are either transparent, translucent or the like.

Still another object of the present invention is a blade-cutting tool for the sizing of longitudinal lengths of blades to predetermined lengths. The blade-cutting tool is a hand-operated device for particular sizing of blades.

Still another object of the present invention is a rotating-disc, fractured-edge blade mounted for rotation in a yoke of a scalpel handle. The circular-disc fractured-edge blade can be either hand driven, such as by rotating the edge over the tissue to be cut or can be mechanically driven for tougher tissue as high-speed operation.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts throughout the figures thereof and wherein.

DESCRIPTION OF PREFERRED EMBODIMENTS

Figure 1:
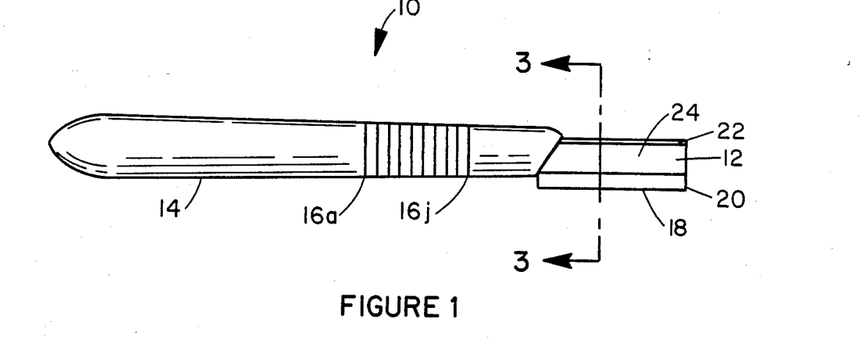
FIG. 1 illustrates a plan view of a glass blade, the present invention.

FIG. 1 illustrates a plan view of a scalpel 10, the present invention, including a blade body 12 as later described in detail, the handle 14 and a plurality of encompassing grooves 16a–16j for holding the handle. FIG. 1 can be referred to as the starboard view. The blade 12 includes one fractured edge 18 which is sharp, thin and smooth and end 20 is planar. The blade body 12 includes the fractured edge 18 by a process later described, and is from glass, crystalline, non-crystalline of composite material. The edge 18, the end 20, and faces of the body of the blade all have predetermined geometrical configurations and can be dependent upon the body of the core from which the blade is fractured. Edge 22 can be either a fractured edge or a plain edge. Faces 24 and 26 of FIG. 3 are substantially planar.

Figure 2:
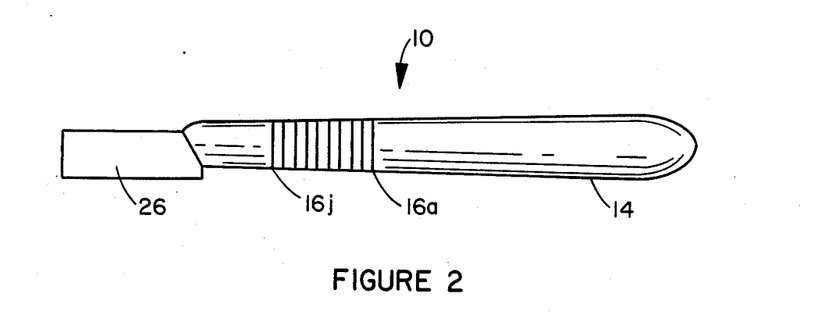
FIG. 2 illustrates a reverse view of FIG. 1.

FIG. 2 shows an obverse view of the scalpel 10. All other numerals correspond to those previously described.

Figure 3:
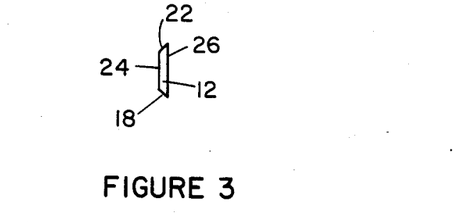
FIG. 3 illustrates a sectional view taken along line 3—3 of FIG. 1.

FIG. 3 illustrates a sectional view taken along line 3—3 of FIG. 1 where all numerals correspond to those numerals previously described.

Figure 4:
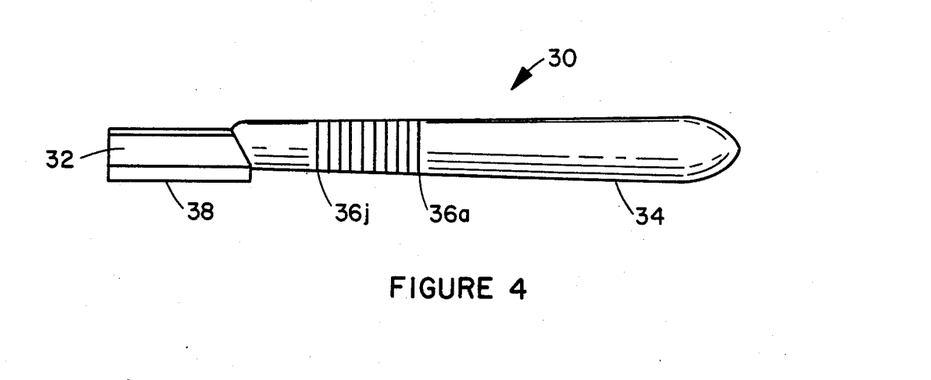
FIG. 4 illustrates a plane view of an obverse of the glass blade of FIG. 1.

FIG. 4 illustrates a plan view of a left-handed blade which is the obverse of FIGS. 1-3. The left-handed scalpel 30 includes the blade 32, the handle 34, the grooves 36a–36j, and the fractured edge 38 as described for FIGS. 1-3 as being similar in structure.

Figure 5:
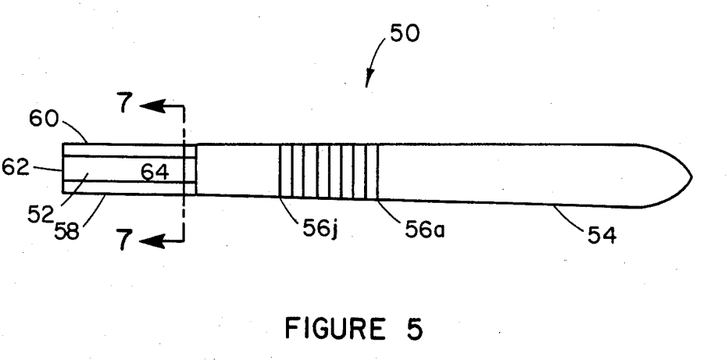
FIG. 5 illustrates a double-edge glass blade.

FIG. 5 illustrates a double-edged scalpel 50 including a double-edged blade 52 later described in detail, a handle 54, and circumferential gripping grooves 56a–56j. Fractured edges 58 and 60 are provided on opposing sides of the blade between the junction of the blade 52 and the handle 54 and the planar end 62. The particular thinness of the blade, angle of the blade, etc., are determined by the geometrical configuration and size of the blade 62 between the substantially planar side surfaces 64 and 66 as well as the core body of material from which the blade body is fractured. The blade, glass in this instance, is secured to the handle with an appropriate glue or adhesive such as epoxy. The geometry of the blade body is also determined by the fracturing process as later described. The blade can also be attached into a socket of a handle through a heat-forming shrinking process.

Figure 6:
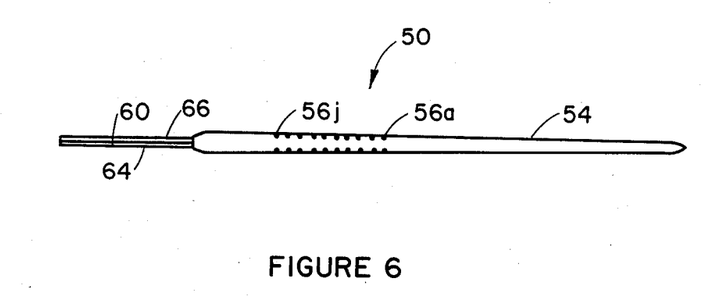
FIG. 6 illustrates a top view of FIG. 5.

FIG. 6 illustrates a top view of the scalpel 50 where all elements correspond to those elements previously described.

Figure 7:
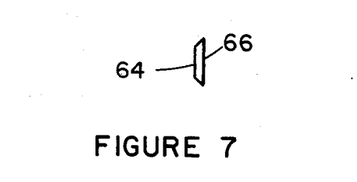
FIG. 7 illustrates a sectional view taken along line 7—7 of FIG. 5.

FIG. 7 illustrates a sectional view taken along line 7—7 of FIG. 5 where all numerals correspond to those elements previously described. This particular scalpel 50 can be used by either a right-handed or left-handed individual.

Figure 8:
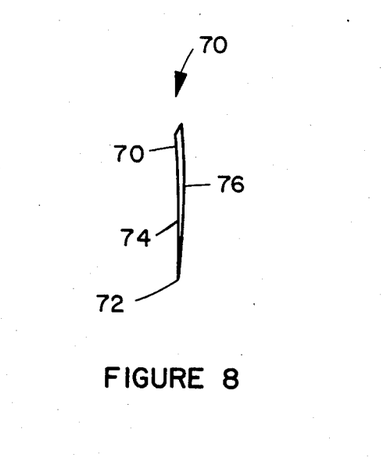
FIG. 8 illustrates a cross-sectional view of a fractured blade.

FIG. 8 illustrates a cross-sectional view of a blade body fractured under tension successfully yielding a very finite, sharp, angular blade 70 having a sharp edge 72 with angular sides 74 and 76. The particular feature of FIG. 8 is the sharpness of the point type edge 72 with respect to sides 74 and 76.

Figures 9, 10:
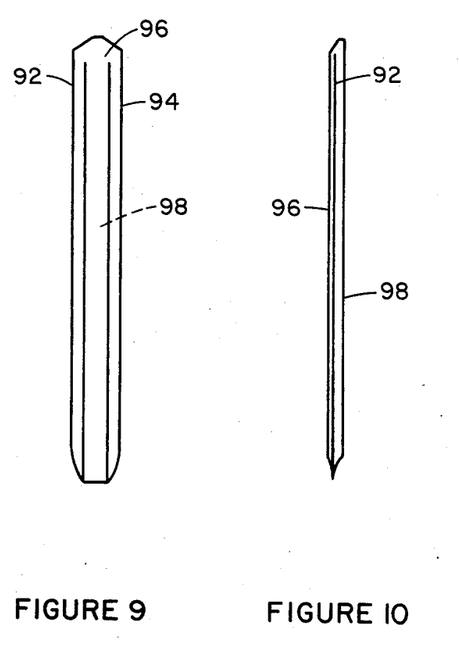
FIG. 9 illustrates a frontal view of a fractured glass blade.
FIG. 10 illustrates a side view of FIG. 9.

FIG. 9 illustrates a front view of a typical fractured blade 90 including in this particular example two fractured edges 92 and 94 between opposing faces 96 and 98. The faces 96 and 98 are particularly smooth. The blade is subsequently cut into segments as later described for affixing to handles or the blade can be used with the substantially configured end with a truncated end.

FIG. 10 illustrates a side view of FIG. 9 where all numerals correspond to those elements previously described. It is noted during fracturing that the distal end of the blade can curve inward, but of course this portion can be cut and discarded although this portion is also usable as a cutting edge as so desired.

Figures 11, 12:
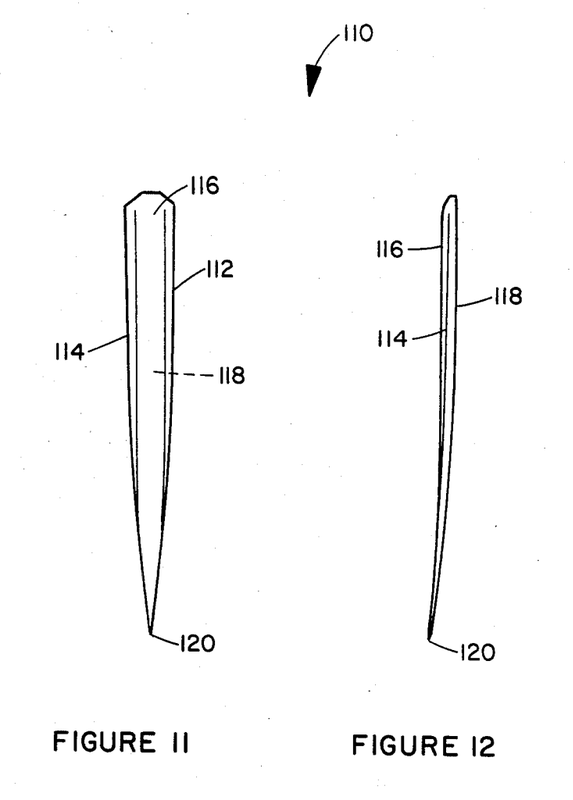
FIG. 11 illustrates a plan view of a pointed glass blade.
FIG. 12 illustrates a side view of FIG. 11.

FIG. 11 illustrates a plan view of a blade 110 including cutting edges 112 and 114 along the length of the opposing sides 116 and 118, all of the edges and sides arriving at and coming to a point 120. The width of the blade, height, and degree of the sharp fractured edges are determined by the particular considerations of use and the core of the body during the fracturing process as later described.

FIG. 12 illustrates a side view of FIG. 11 where all numerals correspond to those elements previously described. There is illustrated a slight curvature of the blade which can vary from a slight degree to a large degree dependent on numerous considerations, or the tip can be planar to the body.

Figure 13:
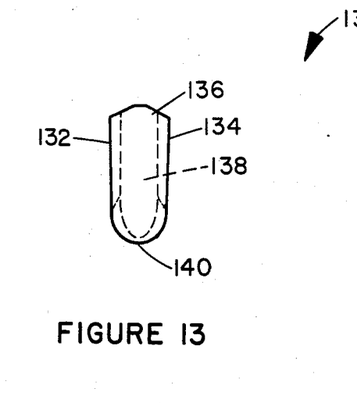
FIG. 13 illustrates a plan view of a rounded glass blade.

FIG. 13 illustrates a plan view of a blade 130 including edges 132, 134 and either a smooth planar, concave or convex surface 136 and an opposing surface of like geometrical or differenti geometrical variation 138. The blade includes a rounded edge 140 where the fractured edges can continue partially down the length of the blade or down to the end of the blades as illustrated in dashed lines.

Figure 14:
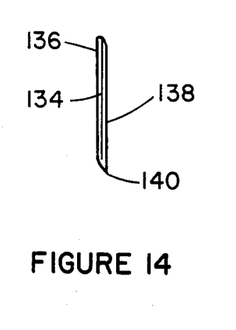
FIG. 14 illustrates a side view of FIG. 13.

FIG. 14 illustrates a side view where all numerals correspond to those elements previously described.

PROCESS OF OPERATION

Blades can be produced from suitable materials, the most common being glass, known as silica dioxide. Blades can also be produced from the group of material including silver bromide, silver chloride, aluminum oxide (sapphire), aluminum oxide+chromium (ruby), multicomponent chalcogenide glass, arsenic trisulfide, arsenic selenide, arsenic trisulfide, barium fluoride, barium titanate, calcite, calcium fluoride, cadmium fluoride, cadmium sulfide, cadmium telluride, cerium trifluoride, chromium oxide, cesium bromide, cesium chloride, cesium fluoride, cesium iodide, CsI sodium modified, iron phosphates, gallium arsenide, gallium oxide, gallium phosphate, gallium antimonide, germanium ge oxide, $Ge_{33}As_{12}Se_{55}$, $Ge_{28}Sb_{12}Se_{60}$, germanium telluride, indium arsenide, indium phosphate, indium antimonide, potassium bromide, potassium chloride, potassium fluoride, potassium iodide, lanthanum fluoride, lithium fluoride, magnesium fluoride, magnesium oxide, Spinel (magnesium aluminate), manganese fluoride, molybdenum oxide, sodium bromide, sodium chloride, sodium fluoride, sodium iodide, sodium nitrate, neodymium trifluoride, nickel oxide, lead chloride, lead fluoride, lead sulfide, lead selenide, lead telluride, $Pd_4Si$, praseodymium trifluoride, rubidium iodide, sulphur, antimony-tellurium, selenium, arsenic mod. selenium, silicon, multi. chal. glass, silica dioxide, tin oxide, strontium fluoride, strontium titanate, tellurium, titanium dioxide, thallium bromide, thallium chloride, $Tl_2Se.As_2Te_3$, vanadium phosphate, tungsten oxide, zinc chloride, zinc fluoride, zinc oxide, zinc sulfide, zinc selenide, zinc telluride, thallium bromoiodide, thallium chlorobromide, lithium chloride, lithium iodate, lithium bromide, rubidium bromide, rubidium chloride, beryllium aluminate, beryllium aluminum silicate, beryllium oxide, cadmium selenide, carbon (diamond), KDP ($KH_2PO_4$), YAG ($Y_3Al_5O_{12}$), GGG ($Gd_3Ga_5O_{12}$), zirconium oxide and potassium oxide. Other like materials can be utilized also which exhibit fracture or the like qualities.

Materials include those which are natural as found in in the ground, materials which have been processed, or materials which are composite such as man-made.

Other materials are within the scope of the teachings of this patent and are not limited to the specific materials disclosed herein, as the teachings are extenable to any suitable material providing for controlling fracturing of the material and thereby providing a sharp fractured edge.

The blades can be processed by a suitable hydraulic press for fracturing of glass, crystalline, non-crystalline or composite material for controlling the holding of the material, and the angle of fracture including the force over a discreet period of time and over a finite area. A hydraulic press would be suitable for controlling during process fracturing materials for blades or other force-pressure systems.

The process for producing glass blades is a function of primary variables, secondary variables, and tertiary variables. The primary variables include the pressure of the shaft fracturing the material, the angle of the shaft fracturing material, the tension between the shaft and the material, the hardness of the material, and the tensile strength and density of the material. The secondary variables include the area of the pressure shaft, the hardness of the pressure shaft, and the duration of loading as a function of pressure over time. The tertiary variable is placement of the pressure shaft with respect to the material which determines the edge or edges of the fractured blade and the geometrical section obtained during the fracturing process. Each of the variables is now defined as the following functions:

(1) $P_{(s)}$ Shaft Pressure $= \dfrac{\text{Pressure shaft tip hardness}}{\text{Pressure shaft tip area}}$ /Material hardness (2) $\quad = \dfrac{PST(H)}{PST(A)}$ /Y kg/MM$^2$ (3) $\angle°$ Angle $= \angle 0° - 30°$ (4) $T$ Tension $=$ (Angle $\times$ Pressure)

(5) $\quad = (\angle° \times P_{(s)})$ (6) $\quad = \left( \angle° \times \dfrac{PST(H)}{PST(A)} / Y \text{ kg/MM}^2 \right)$ (7) $H_{(M)}$ Material Hardness $=$ Y kg/MM$^2$
(8) $T_{(M)}$ Material Tensile Strength $=$ Y lb/in$^2$
(9) $D_{(M)}$ Material Density $=$ Y g/CM$^3$
(10) $PST_{(A)}$ Pressure shaft tip area $= \pi R^2$ (MM)
(11) $PST_{(H)}$ Pressure shaft tip hardness $=$ Y kg/MM$^2$
(12) DL Duration of loading $=$ Pressure/$Time$ (13) $= P_{(s)}/t$ (14) $\dfrac{\frac{PST(H)}{PST(A)} / Y \text{ kg/MM}^2}{t}$ (15) $PST_{(P)}$ Placement of pressure shaft tip Fracturing of the blade, such as from glass, crystalline, non-crystalline or composite material, translucent, transparent or non-transparent, is controlled by a fracturing equation. The specific groups of variables outlined above determine the specific edge, the point, and the geometrical configuration of the opposing surfaces about the blade body. Fracturing is a function of the shaft pressure, angle, tension, material hardness, material density, material tensile strength, pressure shaft tip area, pressure shaft tip hardness, duration of loading, and placement of the shaft tip. These functions are defined in equation 1 as set forth below:

EQUATION 1

$$\text{FRACTURE} = \left[\left(\begin{array}{c}\text{Shaft}\\\text{Pressure}\end{array} \times \text{Angle} \times \text{Tension} \times \begin{array}{c}\text{Matl.}\\\text{Hardness}\end{array} \times \right.\right.$$

$$\left.\begin{array}{c}\text{Matl. Tensile}\\\text{Strength}\end{array} \times \begin{array}{c}\text{Material}\\\text{Density}\end{array}\right) \times \left(\begin{array}{c}\text{Pressure Shaft}\\\text{Tip Area}\end{array} \times\right.$$

$$\left.\left.\begin{array}{c}\text{Pressure Shaft}\\\text{Tip Hardness}\end{array} \times \begin{array}{c}\text{Duration of}\\\text{Loading}\end{array}\right)\right] \times \begin{array}{c}\text{Placement of}\\\text{Shaft Tip}\end{array} \quad \text{eq. 1}$$

The above equation defines substantially the fracturing of an edge under controlled variables as delineated in functions 1–14 as defined above.

Equation 1 can be further defined where fracturing is equal to the functions of the controlled variables as set forth by the relationship:

EQUATION 2

$$\text{FRACTURE} = [(P_{(S)} \times \angle° \times (\angle° \times P_{(S)}) \times H_{(M)} \times D_{(M)} \times$$
$$T_{(M)}) \times (PST_{(A)} \times PST_{(H)} \times P_{(S)}/t)] \times PST_{(P)} \quad \text{eq. 2}$$

where the functions are those of function equations 1–14 previously set forth above.

Finally, fracturing is expressed as being equal to the equations for each of the relationships of functions 1–14 of the controlled variables for shaft pressure, angle, tension, material hardness, material density, material tensile strength, pressure shaft tip area, pressure shaft tip hardness, duration of loading and placement of the shaft tip yielding the relationship denoted as the fracturing equation (fracturing equation 3):

EQUATION 3

$$\text{Fracture} = \left[\left(\frac{PST_{(H)}}{PST_{(A)}}/Y\,\text{kg/MM}^2 \times \angle° \times \left(\angle° \times \right.\right.\right.$$

$$\left.\frac{PST_{(H)}}{PST_{(A)}}/Y\,\text{kg/MM}^2\right) \times Y\,\text{kg/MM}^2 \times Y\,\text{g/CM}^3 \times$$

$$Y\,\text{lb/in}^2\right) \times \left(\pi R^1\,(\text{MM}) \times Y\,\text{kg/MM}^2 \times \right.$$

$$\left.\left.\frac{\frac{PST_{(H)}}{PST_{(A)}}/Y\,\text{kg/MM}^2}{t}\right)\right] \times PST_{(P)} \quad \text{eq. 3}$$

The fracturing equation specifically determines the fractured edge or edges and the geometrical configuration of the blade body dependent upon the material and the other predetermined factors which are controlled during the process.

Figure 15:
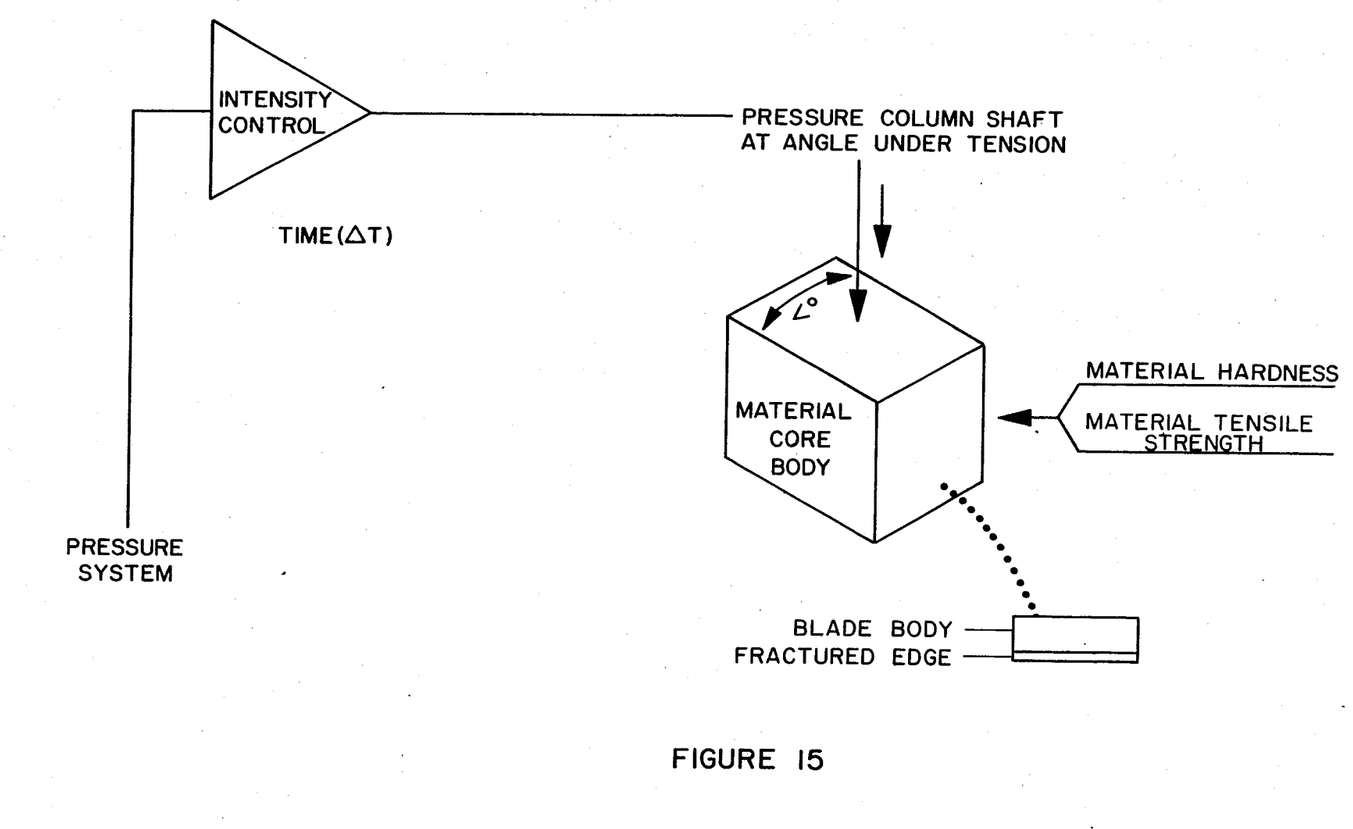
FIG. 15 illustrates a flow diagram of variables for fracturing blades.

FIG. 15 illustrates a system diagram of flow of controlled variable parameters during fracturing of blades from a core of material. The diagram specifically illustrates the variable parameters with respect to material for fracturing a plurality of blades from a core of material. The diagram specifically shows that pressure through a hydraulic system or the like defined specifically through angle, force and time in a column against a core of material yields the fracturing of blades from a core. Numerous apparatuses could be utilized; therefore no specific apparatus is disclosed which is the subject matter of other embodiments.

Material such as glass or any other suitable material including material such as crystalline, non-crystalline, composite or like materials are suitably gripped and viewed during the process, exposing an upper surface to the pressure column. Fracture initiation is under controlled tension, providing for movement of the blade body. Usually more than one distinct motion is required for fracture initiation where the pressure column is peripherally related to the fracture initiation.

Once a definite point of fracture is reached where there is a tension greater tha that not fracturing the material, the fracture develops at a controlled pressure prompting the removal of a blade body. Inherently, controlling the rate of pressure results in the controlled fracture as the pressure increases.

During the fracturing process, the core of the material is advanced forward of the pressure column, initiating new fractured edges for each body in a repetitive manner.

ILLUMINATED BLADE OF A SCALPEL—FIRST ADDITIONAL EMBODIMENT OF THE INVENTION

Figure 16:
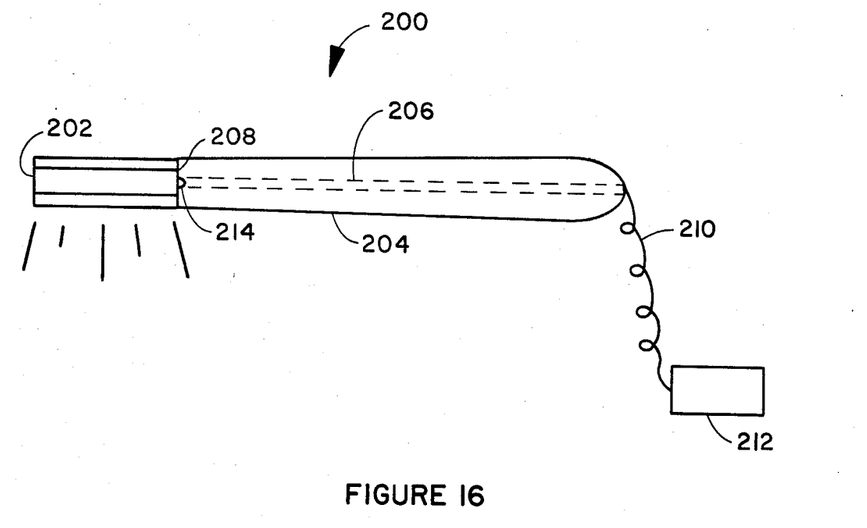
FIG. 16 illustrates a side view of an additional embodiment of an illuminated scalpel.

FIG. 16 illustrates a front view of an illuminated scalpel 200, including a blade 202, a handle 204 being attached to the blade at a blade-handle junction 208 which can be with suitable glues or adhesives, and a slot 206 extending the longitudinal length of the handle 204. An illuminating power cord 210 connects between a power source 212 and an illuminating source 214 positioned at the junction 208 internal to the hole 206. The blade body is transparent, translucent, or the like.

The power cord such as wires or a fiber optic and the power source as a battery or liguht souce can be self-contained in the handle 204 providing for a compact, lightweight handheld scalpel.

Figures 17, 18:
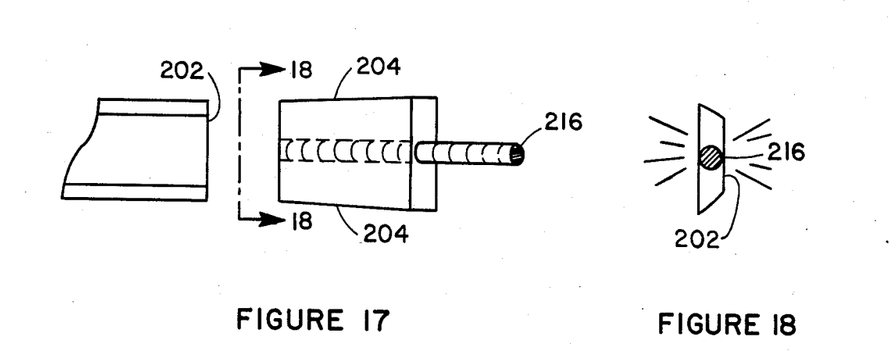
FIG. 17 illustrates a side view of the blade handle junction with the fiber optic illumination.
FIG. 18 illustrates a sectional view taken along line 18—18 of FIG. 17.

FIG. 17 illustrates a side view of blade 202-handle 204 including a fiber optic strand or cable bundle 216 including the polished end representing the illuminating source 214. Accordingly, the power cord 210 represents a strand or cable bundle of fiber optics connected to an illuminating power source 212. The fiber optic illuminates energy exciting light through the blade, the edges, subsequently providing for internal illumination of the blade and illuminating the area about the blade. Accordingly, the blade or light energy can be color coded for different types of surgery or different uses of the blade in surgery.

FIG. 18 is a view taken along line 18—18 of FIG. 17 and shows a front view of the handle.

Figure 19:
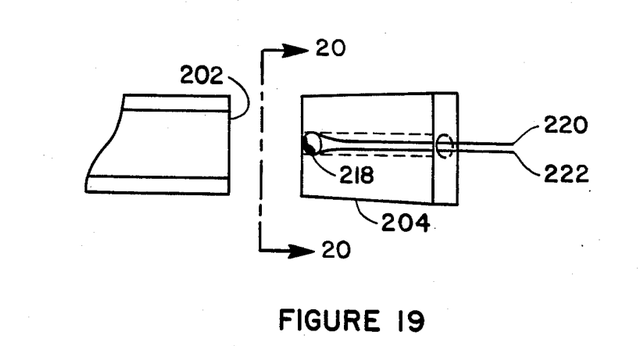
FIG. 19 illustrates a side view of a blade-handle junction with an LED or grain-of-wheat illumination source.

FIG. 19 illustrates a side view similar to FIG. 17 where an LED 218 including two wires 220 and 222 extends from the junction 208 back through the handle, out the end of the handle through the illumination power cord 210 which would include two wires, and to a low-voltage power source 212. The LED 218 represents the illuminating source at the end of the handle 214 and operates identically to that of FIG. 17 as previously described.

Figure 20:
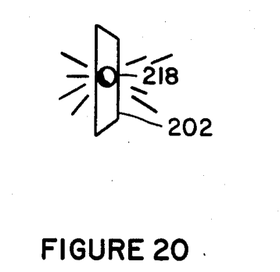
FIG. 20 illustrates a view taken along line 20—20 of FIG. 19.

FIG. 20 illustrates a view taken along line 20—20 of FIG. 19 where all numerals correspond to those elements previously described and is likewise similar in operation to that previously set forth in FIG. 18.

One preferable embodiment in light of the present invention would include a power source in the handle such as a plurality of cells, a light generating source, and a fiber optic or optics to transmit the light to the blade. The handle can be easily heat formed about the power source-power souce such as battery or piezoelectric—fiber optic or optics—and the blade. Such an illuminated blade provides an compact scapel to the surgeon without attachments to a power source, etc.

ADDITIONAL EMBODIMENT MODE OF OPERATION

The illuminated glass blade, where the blade can be transparent or translucent material besides glass, provides for illumination of the area about a surgical incision. The illumination through the transparent blade eliminates the problems which have been associated with the prior art external sources of illumination including bulkiness, interfering projections, shadows, eye fatigue of the surgeon, and non-visibility of tissue. The illuminated transparent blade provides for improved visibility of an incision and the availability of multi-colored illumination enhancing the surgeon's view. The intensity and color of the illuminating light can be varied and adjusted through the selection of the appropriate illuminating source.

INTERCHANGEABLE BLADE—SECOND ADDITIONAL EMBODIMENT

Figure 21:
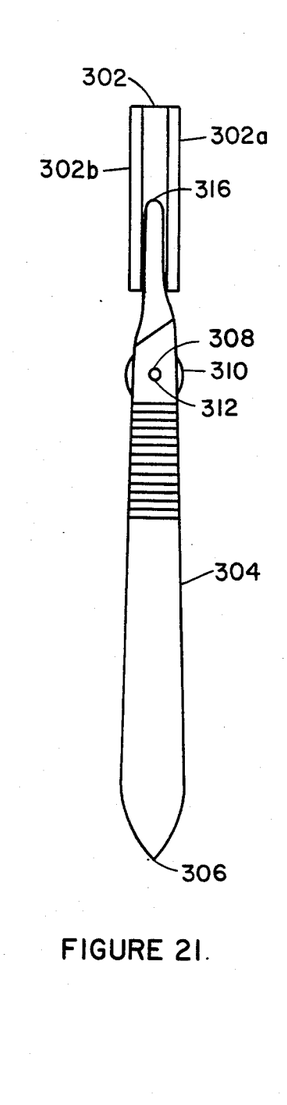
FIG. 21 illustrates a front view of an interchangeable blade holder for interchanging the blades.
Figure 22:
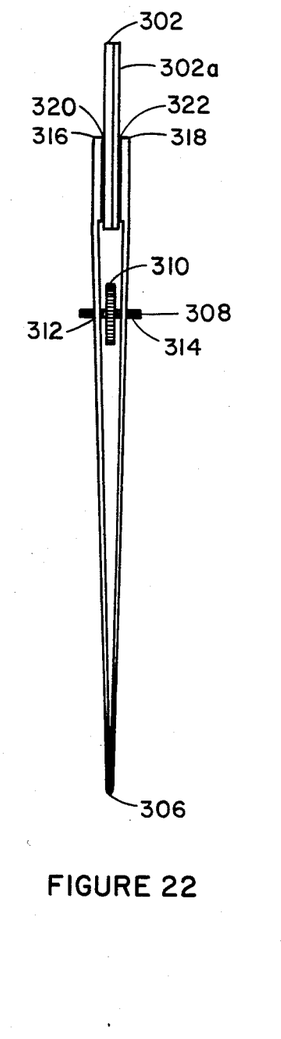
FIG. 22 illustrates a side view of the blade holder.

FIG. 21 illustrates a front view of an interchangeable blade alternative embodiment of the present invention. The interchangeable blade system 300 includes an interchangeable blade body 302, a caliper rip device 304 secured at one end in a tweezer-like fashion 306, and including a threaded rod 308 having a thumb wheel 310 affixed between threaded points 312 and 314 as also illustrated in FIG. 22. Pointed ends 316 and 318 of FIG. 22 secure the blade body 302 having at least a fractured edge 302a and in this instance 302b, either between the edges or including a gripping surface such as rubber-like compound 320 and 322 illustrated in FIG. 22.

While the blade here is illustrated as a substantially rectangular blade body with substantially opposing parallel surfaces, this is by way of example and for purposes of illustration only and not to be construed as limiting of the present invention. Any suitable blade body can be secured within the interchangeable blade assembly system and further, support and gripping of the interchangeable blade body can be accomplished through the configured rubber members 320 and 322 secured to the sides 316 and 318.

FIG. 22 illustrates a side view of FIG. 21 where all numerals correspond to those previously described.

INTERCHANGEABLE BLADE ALTERNATIVE EMBODIMENT MODE OF OPERATION

The blade body 302 is appropriately gripped by the force action positioned by the thumb screw 310 through the threaded rod 308 and the threaded holes 312 and 314. The opposing force by the members 316 and 318 acting through the bottom 306 compresses and frictionally engages the blade body 302 in a fixed position.

BLADE-CUTTING TOOL—THIRD ADDITIONAL EMBODIMENT OF THE INVENTION

Figure 23:
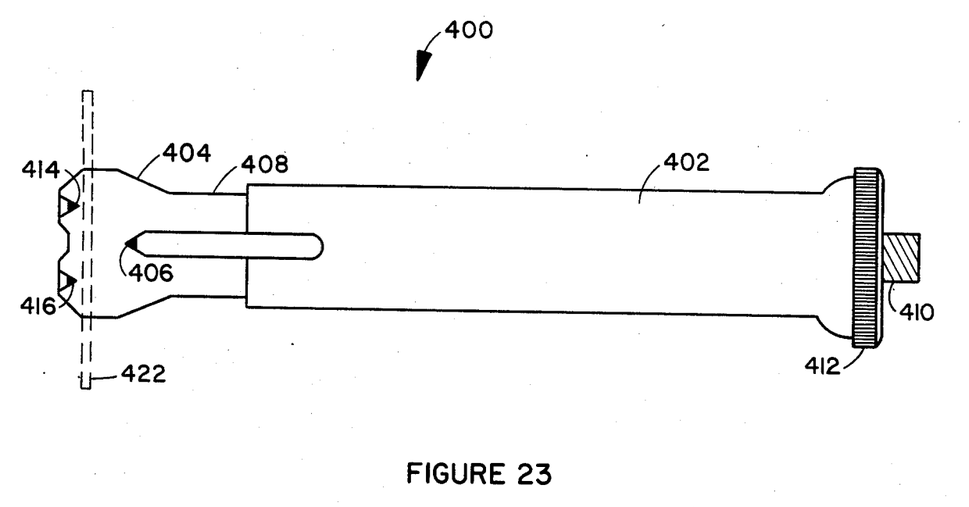
FIG. 23 illustrates a top view of a blade-cutting tool.

FIG. 23 illustrates a top view of a blade-cutting tool 400 including a hollow cylindrical shaft 402 expanding outwardly toward the distal end 404. A hard point 406 attaches the main body of the tool 400. Within the main body is a solid, free-moving shaft 408 encircled by a spring 410 illustrated in FIG. 24. The distal end of the shaft as threaded at 410 protrudes out the rear of the main body. A threaded, knurled disc 412 is attached to the end of the threaded shaft 410 and abuts the rear of the main body 402. An opposite end of the shaft 408 expands outward and incorporates two hard points 414 and 416. A handle 418 secures to the shaft 402 and pivots at 420.

Figure 24:
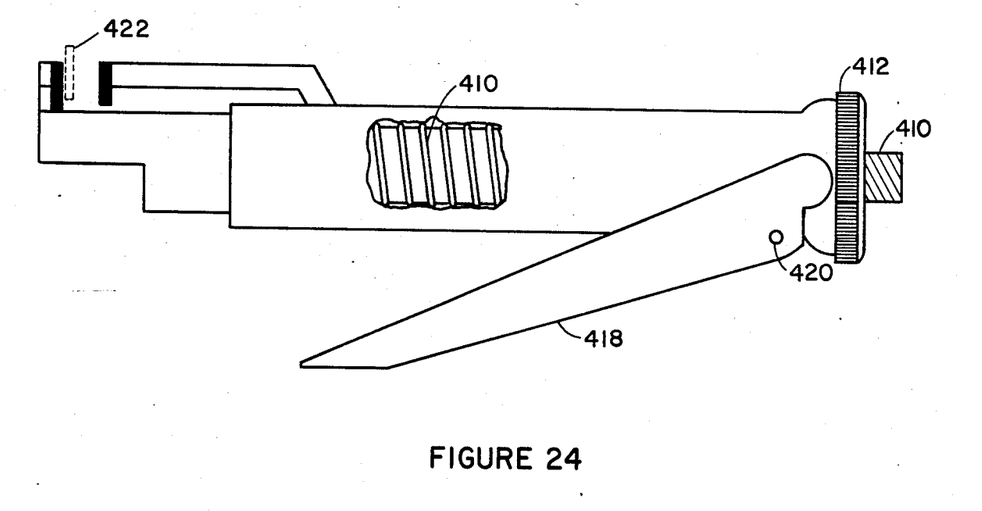
FIG. 24 illustrates a side view of FIG. 23.

FIG. 24 illustrates a side view of FIG. 23 where all numerals correspond to those elements previously described.

MODE OF OPERATION OF BLADE-CUTTING TOOL

Adjustment of the knurled disc 412 opens or closes a gap between the hard pointts 414, 416 and 406. When an appropriate size gap has been attained, a blade 422 is positioned between the points and the single point 406 defining the area at which the cutting will occur. Squeezing the handle 418 pulls the shaft 408 through the hollow shaft 402, thereby causing pressure to be exerted upon the blade between the points, gradually increasing the pressure which eventually causes cutting from tension on the side of the blade opposite the point 406. Once the blade is cut, the release of handle 418 releases the pressure through the internal spring 410 thereby returning the shaft 408 to its original position.

SCALPEL WITH CIRCULAR DISC BLADE—FOURTH ADDITIONAL EMBODIMENT OF THE INVENTION

Figure 25:
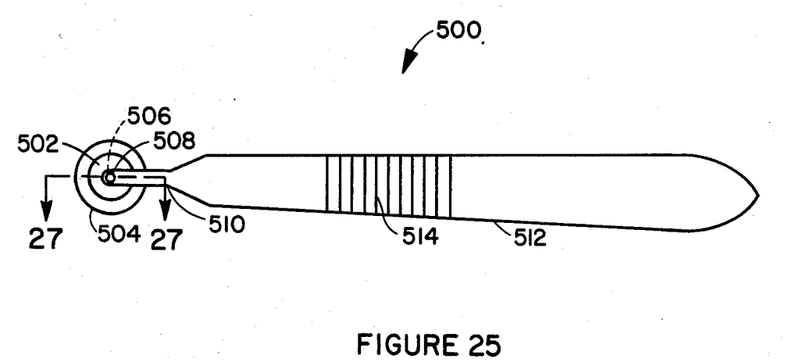
FIG. 25 illustrates a side view of a rotary blade scalpel.

FIG. 25 illustrates a side view of a scalpel 500 with a circular disc blade 502. The circular disc blade 502 includes a fractured edge 504, the circular disc 502 and the fractured edge 504 being in a geometrical, symmetrical relationship with respect to each other. The fractured edge has a finite cutting edge angle 504a as well as an edge profile angle 504b, both of the angles illustrated in FIG. 27. A hole 506 is provided through the disc 502 and a shaft 508 secures between both sides of a yoke 510. The yoke 510 is affixed to a handle 512, the handle including a plurality of grooves 514 for gripping of the handle. The disc 502 can either rotate freely about the shaft 508, or in the alternative the shaft and disc can be secured together such as by glue or the like and the shaft can rotate freely in the yoke 510.

Figure 26:
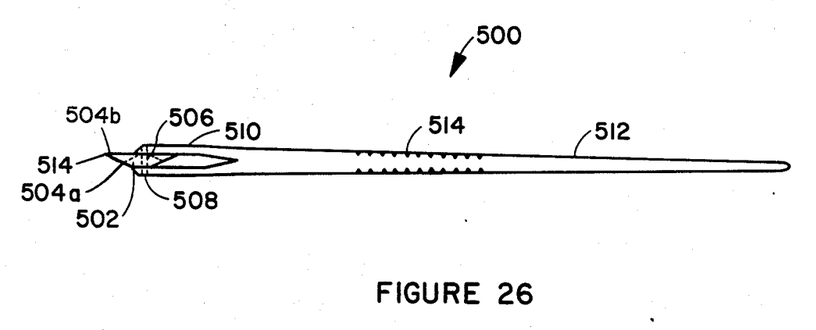
FIG. 26 illustrates a top view of FIG. 25.
Figure 27:
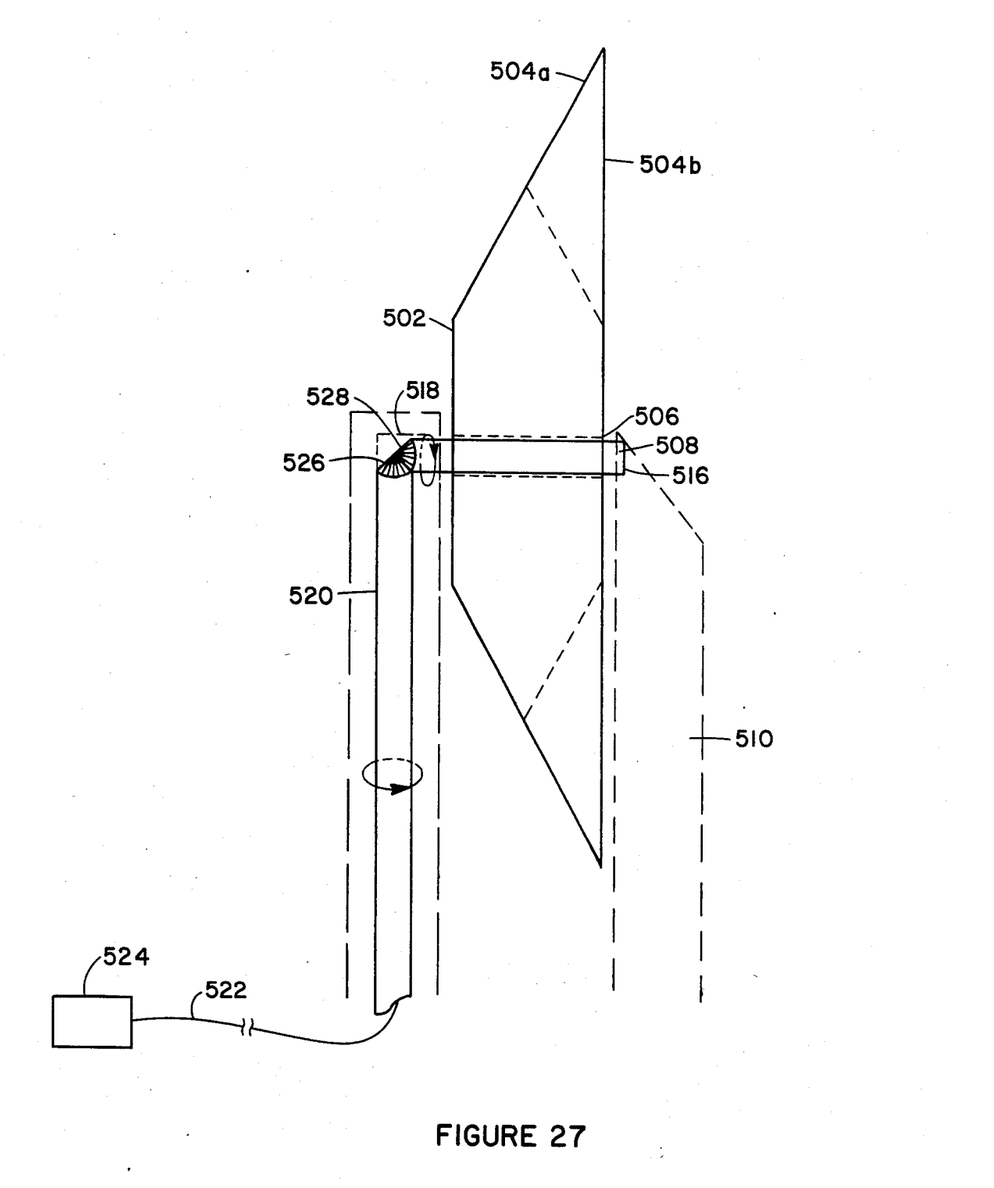
FIG. 27 illustrates a view taken along line 27—27 of FIG. 25.

FIG. 27 illustrates a slightly modified alternative embodiment of FIGS. 25 and 26 where the rotating disc 502 is powered by a suitable power source. The shaft 508 freely mounts in the hole 506 and into a shaft socket 516 and through an other side of the yoke in a socket member 518. A power shaft 520 is mounted in the yoke 510 and can extend through the handle, through a power cord 522 to a power supply 524. The rotating shaft 520 is appropriately supported for rotation through the yoke and the handle 512 of the scalpel 500. The power cord can be a suitable arrangement similar to that of dentist's drills, being either electromechanical or hydraulic in the power drive source. For purposes of expediency, etc., the yoke members can provide enough flexibility for separation to replace different sizes of rotating discs or rotating discs with different cutting angles, the cutting angles being that of the fractured edges, as so desired and predetermined by the surgeon. Gears 526 and 528 impart right angular drive to the shaft which has the rotating disc secured thereto, but a flexible drive shaft could also be utilized. The gears can be pyramidal gears or the like mechanical structure for providing right angular drive.

The disc blade 502 can be process through a conical fracturing process, similar to that of a bullet through a glass pane principal. This will produce a desired circular disc blades as that illustrated in the FIGS. 26 and 27.

Various modifications can be made to the present invention without departing from the apparent scope thereof.

Having thus described the invention, what is claimed is:

1. Process of fracturing a glass blade, said process comprising:
    a. securing a core of glass, crystalline, non-crystalline or composite material;
    b. positioning an edge of said core of said material at a predetermined angle to a pressure shaft;
    c. forcing said pressure shaft against said core at a predetermined pressure, at a predetermined velocity, at said predetermined angle over a time interval; and
    d. increasing said force initiating fracture of a blade body whereby said blade includes a fractured edge thereby providing a smooth and sharp cutting edge.
2. Process of claim 1 comprising:
    a. adjusting tension as a function of angle and pressure and as a function of material hardness and material density.
3. Process of claim 1 comprising:
    a. adjusting the duration of loading as a function of pressure over time.
4. Pressure of claim 1 comprising:
    a. fracturing the material according to the variable parameters delineated as the pressure of the shaft fracturing the material, the angle of the shaft fracturing material, the tension between the shaft and the material, the hardness of the material, the tension strength and density of the material, the area of the pressure shaft, the hardness of the pressure shaft, duration of loading as a function of pressure over time, and placement of the pressure shaft with respect to the material which determines the edge or edges of the fractured blade and the geometrical section obtained during the fracturing process.
5. Process of claim 1 wherein said core determines said fractured edge.
6. Process of claim 1 whwerein said core determines an end of said blade body.
7. Process of claim 1 comprising the step of repetitively fracturing blades from said core.
8. Blade with at least two fractured edges by the process of claim 1.
9. Blade with at least one fractured edge by the process of claim 1.

* * * * *